United States Patent [19]

Cole

[11] Patent Number: 4,743,239
[45] Date of Patent: May 10, 1988

[54] DISPOSABLE BRIEF HAVING AN AREA OF RELATIVELY THIN ABSORBENT MATERIAL AND AN AREA OF RELATIVELY THICK ABSORBENT MATERIAL

[76] Inventor: Shelley K. Cole, 4505 W. North La., Glendale, Ariz. 85302

[21] Appl. No.: 928,021

[22] Filed: Nov. 7, 1986

[51] Int. Cl.⁴ .......................................... A61F 13/16
[52] U.S. Cl. .................................. 604/385 R; 604/396
[58] Field of Search ...................... 604/385.1, 394, 396

[56] References Cited

U.S. PATENT DOCUMENTS 3,237,625  3/1966  Johnson .............................. 604/396
4,619,649  10/1986  Roberts .............................. 604/396

*Primary Examiner*—John D. Yasko
*Attorney, Agent, or Firm*—H. Gordon Shields

[57] ABSTRACT

Disposable brief includes an exterior moisture barrier and an interior area having two different absorbent materials, including a relatively thin layer of absorbent material and a center portion having a relatively thick layer of absorbent material. The sides of the brief are perforated to enable the brief to be easily removed after an accident by the user of the brief. The waist and legs are elasticized.

9 Claims, 1 Drawing Sheet

U.S. Patent   May 10, 1988   4,743,239
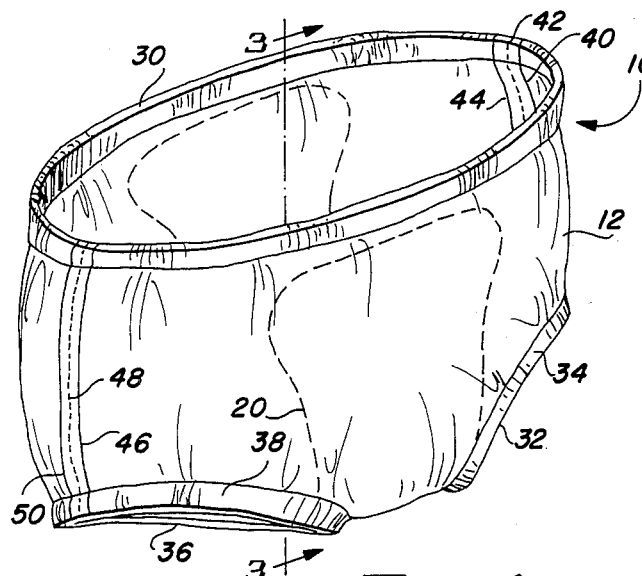
FIG. 1
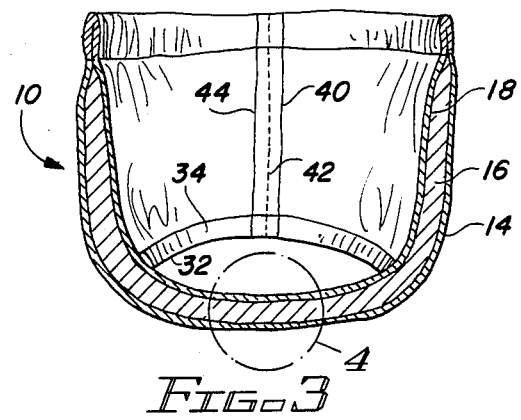
FIG. 3
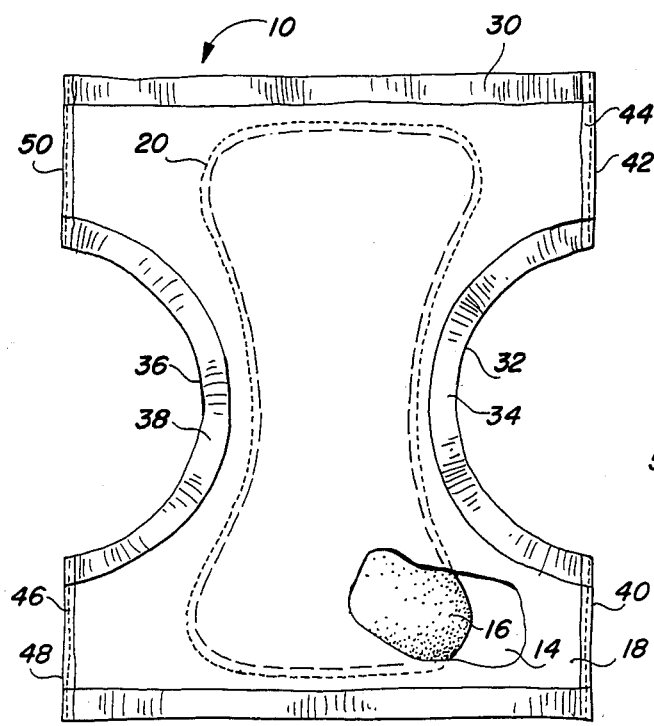
FIG. 2
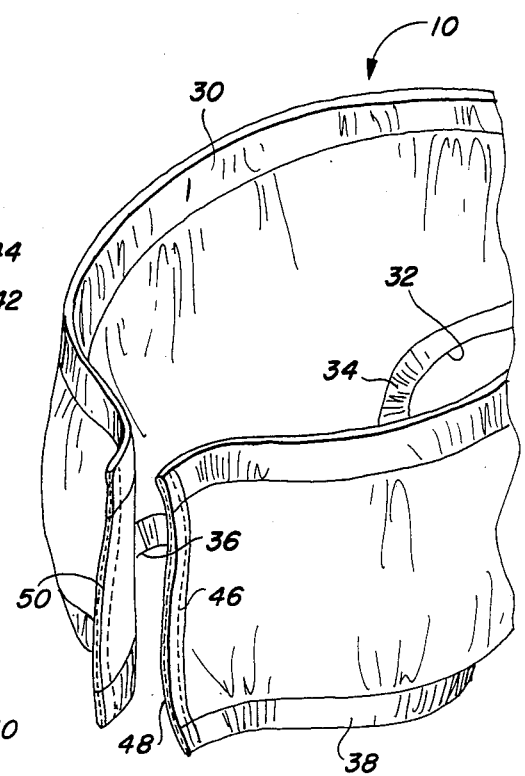
FIG. 5
FIG. 4
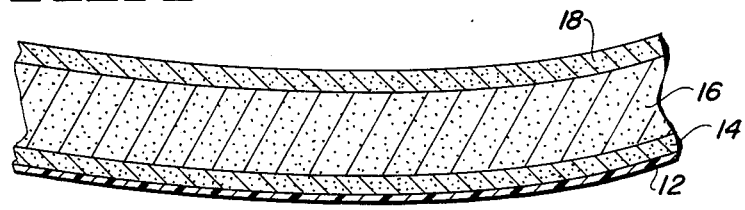

DISPOSABLE BRIEF HAVING AN AREA OF RELATIVELY THIN ABSORBENT MATERIAL AND AN AREA OF RELATIVELY THICK ABSORBENT MATERIAL

BACKGROUND OF THE INVENTION

1. Field of the Invention

This invention relates to disposable garments and, more particularly, to a disposable brief designed as a training garment for young children, for bedwetting, or for use by incontinent adults.

2. Description of the Prior Art

Disposable diapers are well known and understood in the art. They essentially comprise a single piece unit with a waterproof exterior or outer grament and a relatively thick absorbent lining on the inside of the waterproof outer barrier. The area of the diaper designed to accommodate the legs and the waist of the user include elasticized material to help seal the diaper against leakage. To fasten opposite ends of the diaper together, as at the waist of the user, there are adhesive tabs. Any particular diaper can accommodate, within reason, various sized users. Different sized diapers accordingly may accommodate a relatively large range of sizes. The diapers are used for infants, and in very large sizes, for incontinent adults.

When a child "graduates" from the infant stage and begins toilet training, it is generally desirable to eliminate the diaper from regular use for several reasons. One reason is for convenience and ease of use by the child, itself. Another reason is that the child psychologically wants to be viewed as something other than a baby. Moreover, the adults generally wish to view the child, or to have the child believe, that it is other than a baby in order to encourage toilet training.

The next step away from a diaper comprises a so-called training panty. The training panty is generally nothing more than a thick cloth brief. The child is able to remove the cloth training brief rather easily, without having to lie down or be put on a changing table. Thus, the ease of use encourages the child in its toilet training.

While the traditional cloth training brief is usable with a child, it is relatively inconvenient in case of an accident, as by either a bowel accident or a bladder accident. The inconvenience results because the cloth training brief must be removed from the legs of the child. That is, the brief must traverse the entire length of the child's legs in order to remove it. Moreover, while the brief is being removed, the part of the body originally subjected to the accident contaminates the area around the child, such as the bed, the carpet, etc. Furthermore, contamination of the hands of the individual helping the child also occurs. The "contamination" may not be too bad at home, but the contamination may be a substantial problem away from home, and particularly at day care centers. Obviously, the difficulty of the cleanup process is increased due to the inconvenience of the training brief. Finally, there is the question of cleaning and storing the cloth training briefs. This issue is also particularly meaningful away from home, and again particularly at day care centers.

The apparatus of the present invention overcomes the limitations and problems of the prior art by providing a disposable training brief of undergarment with the best features of both a disposable diaper and a traditional cloth brief.

SUMMARY OF THE INVENTION

The invention described and claimed herein comprises a disposable brief which includes an outer lining of generally waterproof material to comprise a moisture barrier and two inner layers, one of which is a relatively thin absorbent layer and the other of which is a relatively thick absorbent layer. The sides of the training brief are perforated or scored so that in case of an accident the brief may be removed without traversing the length of the legs of the user.

Among the objects of the present invention are the following:

To provide new and useful disposable brief;

To provide a new and useful disposable undergarment;

To provide new and useful undergarment having a waterproof exterior lining and absorbent material inside the outer lining;

To provide new and useful brief having scored sides to allow the brief to be opened;

To provide new and useful disposable training brief; and

To provide new and useful disposable brief having a relatively absorbent layer secured to a relatively waterproof outer layer with scored sides which allow the brief to be opened and removed relatively easily.

BRIEF DESCRIPTION OF THE DRAWING

FIG. 1 is a perspective view of training briefs embodying the present invention.

FIG. 2 is a plan view of the training briefs of FIG. 1 laid out flat for illustrative purposes.

FIG. 3 is a view in partial section taken generally along line 3—3 of FIG. 1.

FIG. 4 is an enlarged view in partial section of the training briefs taken generally from Circle 4 of FIG. 3.

FIG. 5 is a perspective view of the training briefs of the present invention illustrating a particular feature.

DESCRIPTION OF THE PREFERRED EMBODIMENT

FIG. 1 is a perspective view of a training brief 10 of the present invention. The training brief 10 is disposable and is adapted to be put in the conventional manner of a brief or panty, and to be removed from a child by either of two methods or ways. The first way is the conventional way, in which the disposable training brief 10 is simply removed by sliding the brief downward along the legs of the child. The second way is to tear the briefs on the outer sides of the legs and then to remove the briefs as if it were a diaper.

The disposable training brief 10 includes an outer, generally moisture impermeable layer 12, which is typically made of some appropriate type of plastic, such as polyethylene, or the like. The brief includes an elastic waistband 30, a left leg opening 32, and a right leg opening 36. An elastic band 34 is disposed about the left leg opening 32, and an elastic band 38 is disposed about the right leg opening 36. The elastic bands 34 and 38 hold the brief snugly against the leg of the child. Similarly, the elastic waistband 30 holds the training brief 10 snugly about the child's waist to hold the brief in place.

Extending from the left leg opening 32 upwardly to the elastic waistband 30 is a plurality of perforations 42. The perforations 42 extend through the outer, impermeable layer 12. A similar plurality of perforations 48 extend between the elastic waistband 30 and the right leg opening 36. The perforations 42 and 48 extend through the outer layer 12 at the elastic waistband 30 and also through the outer layer 12 at the respective elastic bands 34 and 38 for the left leg opening and the right leg opening, respectively. The purpose of the perforations 42 and 28 is to allow the training brief 10 to be removed from a child who has had an accident. By tearing the outer layer 12 along perforations 42 and 48, the training brief may be opened up, as shown in FIG. 2, for easy removal of the training brief 10 from the child. The respective elastic bands 30, 34, and 38 stop short of the perforations 42 and 48 through the outer layer 12. This will be discussed in detail below.

FIG. 2 is a plan view of the training brief 10 after the training brief has been "opened" by tearing along the perforations 42 and 48 at the left and right sides, respectively, of the training brief 10. With the training brief 10 opened, as shown in FIG. 2, the training brief may be easily removed, as if it were a diaper, from the child.

FIG. 3 is a view in partial section of the training brief 10 taken generally along line 3—3 of FIG. 1. FIG. 4 is an enlarged view in partial section of a portion of the training brief 10 taken generally from Circle 4 of FIG. 3. FIGS. 3 and 4, and to a lesser extent FIGS. 1 and 2, illustrate the construction of the training brief 10 with respect to the absorbent layers incorporated into the training brief 10.

Adjacent to the outer, impermeable, layer 12 is a relatively thin absorbent layer 14. The relatively thin absorbent layer 14 is continuous and extends over the total outer area of the training brief except for the waistband 30 and the leg bands 34 and 38. In addition, the outer absorbent layer 14 also terminates at side zones which are disposed adjacent to the side perforations 42 and 48. This is best illustrated in FIG. 2.

Adjacent to the plurality of perforations 42 are two side zones 40 and 44. The side zone 40 is a "front" side zone and the side zone 46 is a "rear" side zone. The opposite side of the training brief, adjacent to the perforations 48, also includes a pair of side zones, including a front side zone 46 and a rear side zone 50. The side zones are simply the locations at which the absorbent layers and the elastic bands terminate so as to leave the areas adjacent to the perforations 42 and 48 free from additional thickness or mass which would hinder or inhibit the tearing of the briefs along the perforations for easy removal.

In addition to the thin outer absorbent layer 14, there is a second absorbent layer, which is an inner thin absorbent layer 18. The inner absorbent layer 18 and the outer absorbent layer 14 are both relatively thin and are disposed adjacent to each other to provide two absorbent layers from the training briefs 10. The absorbent layers 14 and 19 are coextensive, and both terminate adjacent to the side zones 40, 44, and 46, 50, as described above for the outer absorbent layer 12.

In addition to the relatively thin outer absorbent layer 14 and the relatively thin inner absorbent layer 18, there is a center absorbent pad or layer 16 in the central or center portion of the training brief 10. The center absorbent layer 16 is relatively thick and is disposed in the area of the training brief 10 most likely to receive urine and feces material in case of an accident from the user or child wearing the training brief 10. The relatively thick center absorbent pad 16 is stitched between the inner and outer layers 12 and 18 to hold it in place. Stitching 20 is shown in FIGS. 1 and 2 outlining the area of the relatively thick, and relatively highly absorbent pad 16. The stitching 20, coextensive with the absorbent layer 16, is in the general configuration of an hour glass.

FIG. 5 is an enlarged perspective view of the training brief 10 showing the brief 10 torn along the perforations 48 for easy removal of the training brief 10. Since there is not absorbent material in the side zones 46 and 50, the brief is easily torn along the perforations 48 to remove the training brief 10 from a child.

Obviously, the training brief 10 may be made in a variety of sizes. Typically, a regular size and a large size may be sufficient. In addition, it may be desirable to eliminate the inner relatively thin absorbent layer 18, particularly in larger sizes, since older children are less likely to have accidents than younger children. In such case, the relatively thick center absorbent layer 16 may be stitched directly to the relatively thin outer absorbent layer 14 and, perhaps, to the outer impermeable layer 12, if desired.

The relatively thick absorbent layer 16, is, of course, relatively soft, and thus will not chafe a child's body if it is employed directly against the child's body without the relatively thin absorbent layer 18.

In the alternative, the relatively thin outer layer 14 may be omitted, and the relatively thick layer 16 may be stitched directly to the inner layer 18. If desired, the outer layer 12 may also be included in the stitching.

While the principles of the invention have been made clear in illustrative embodiments, there will be immediately obvious to those skilled in the art many modifications of structure, arrangements, proporations, the elements, materials, and components used in the practice of the invention, and otherwise, which are particularly adapted for specific environments and operative requirements without departing from those principles. The appended claims are intended to cover and embrace any and all such modifications, within the limits only of the true spirit and scope of the invention. This specification and the appended claims have been prepared in accordacne with the applicable patent laws and the rules promulgated under the authority thereof.

What I claim is:

1. A disposable training brief comprising, in combination:
   outer impermeable layer means;
   first absorbent layer means, including a first relatively thin outer absorbent layer and a first relatively thin inner absorbent layer, substantially coextensive with the outer impermeable layer;
   second absorbent layer means including a relatively thick absorbent layer secured to the first absorbent layer means and disposed between the first outer absorbent layer and the first inner absorbent layer for providing a relatively highly absorbent layer;
   waist band means for securing the training brief to a user;
   leg band means through which the user's legs extend;
   perforation means extending from the leg band means to the waist band means through the outer impermeable layer means for tearing the outer impermeable layer means for removing the training brief in case of an accident by the user, and
   side zones on the outer impermeable layer means adjacent to the perforation means at which the first absorbent layer means terminates.

2. The article of claim 1 in which the second absorbent layer means is secured to the first absorbent layer means remote from the side zones.

3. The article of claim 2 in which the first absorbent layer means comprises an outer absorbent layer and an inner absorbent layer, and the second absorbent layer means is disposed between the outer and inner absorbent layers.

4. The article of claim 1 in which the first and second absorbent layer means are stitched together.

5. The article of claim 1 in which the waist band means includes elastic material for holding the training brief to the user.

6. The article of claim 1 in which the leg band means include elastic material for holding the training brief to the user's legs.

7. The article of claim 1 in which the leg band means includes a left leg hole and a right leg hole, and the perforation means includes first perforations extending between the left leg hole and the waist band means and second perforations extending between the right leg hole and the waist band means to facilitate the tearing of the outer impermeable means to remove the training brief from a user in case of an accident.

8. The article of claim 7 in which second absorbent layer means is in the general configuration of an hour glass.

9. The apparatus of claim 1 in which:
the leg band means includes a left leg hole and a right leg hole;
the outer impermeable layer means includes a first side zone extending from the left leg hole to the waist band means and a second side zone extending from the right leg hole to the waist band means;
the waist band means includes elastic means extending between the side zones; and
the perforation means includes a plurality of perforations extending through the first and second side zones.

* * * * *